United States Patent
Lee et al.

(10) Patent No.: US 9,345,607 B2
(45) Date of Patent: May 24, 2016

(54) CONFIGURABLE SUBSHELL COMPONENTS IN ORTHOPEDIC DEVICES

(71) Applicant: OSSUR HF, Reykjavik (IS)

(72) Inventors: Jane Lee, Fullerton, CA (US); Yessenia Lopez, Cypress, CA (US); Joshua Kompa, Trabuco Canyon, CA (US); Arni Thor Ingimundarson, Gardabaer (IS)

(73) Assignee: OSSUR HF, Reykjavik (IS)

( * ) Notice: Subject to any disclaimer, the term of this patent is extended or adjusted under 35 U.S.C. 154(b) by 108 days.

(21) Appl. No.: 14/282,123

(22) Filed: May 20, 2014

(65) Prior Publication Data

US 2014/0257158 A1    Sep. 11, 2014

Related U.S. Application Data

(63) Continuation of application No. 13/212,382, filed on Aug. 18, 2011, now Pat. No. 8,740,829.

(60) Provisional application No. 61/515,502, filed on Aug. 5, 2011, provisional application No. 61/375,380, filed on Aug. 20, 2010, provisional application No. 61/375,392, filed on Aug. 20, 2010.

(51) Int. Cl.
*A61F 5/00* (2006.01)
*A61F 5/01* (2006.01)

(52) U.S. Cl.
CPC .............. *A61F 5/0102* (2013.01); *A61F 5/0123* (2013.01); *A61F 2005/0172* (2013.01); *A61F 2005/0181* (2013.01)

(58) Field of Classification Search
CPC ........... A61F 5/0123; A61F 2005/0174; A61F 2005/0139; A61F 5/0102; A61F 2005/0181; A61F 5/0125; A61F 2005/0137; A61F 5/0111; A61F 2005/0172; A61F 2005/0167; A61F 2005/0179; A61F 2/60; A61F 13/15203; A61F 13/42; A61F 13/49011; A61F 13/505; A61F 13/532; A61F 13/535; A61F 13/539; A61F 13/84; A61F 13/8405; A61F 13/20; A61F 13/26; A61F 2002/30617; A61F 2002/3071
USPC ................................ 602/16, 23–28; 128/882
See application file for complete search history.

(56) References Cited

U.S. PATENT DOCUMENTS

| 689,991 A | 12/1901 | Rubin |
| 828,573 A | 8/1906 | Rubin |

(Continued)

FOREIGN PATENT DOCUMENTS

| WO | 01/89434 A1 | 11/2001 |
| WO | 03/065942 A1 | 8/2003 |

(Continued)

OTHER PUBLICATIONS

Product Information Sheet, "Defiance, Ideal Application, dj Orthopedics," obtained prior to Aug. 20, 2010, 1 page. Retrieved at www.djortho.com.

(Continued)

*Primary Examiner* — Michael Brown
(74) *Attorney, Agent, or Firm* — Workman Nydegger

(57) ABSTRACT

A coupling device for an orthopedic brace includes an anchoring member for securing to a frame and protruding therefrom, and a subshell arranged to connect to the frame by the anchoring member. The subshell has a locking element for selectively positioning the subshell on the frame at a plurality of locations. The subshell may include an end portion or contoured edge extending beyond a portion of the frame so as to flex relative to the frame.

16 Claims, 10 Drawing Sheets

(56) References Cited

U.S. PATENT DOCUMENTS

| | | | |
|---|---|---|---|
| 1,153,334 | A | 9/1915 | Oswald |
| 2,615,218 | A | 10/1952 | Ross |
| 2,636,234 | A | 4/1953 | Reiter |
| 3,575,166 | A | 4/1971 | Rosman et al. |
| 3,669,105 | A | 6/1972 | Castiglia |
| 3,696,288 | A | 10/1972 | Carman |
| 3,853,071 | A | 12/1974 | Snyder et al. |
| 3,926,186 | A * | 12/1975 | Nirschl ............... A61F 5/0106 602/62 |
| 4,241,730 | A | 12/1980 | Helfet |
| 4,271,999 | A | 6/1981 | Stravitz |
| D284,702 | S | 7/1986 | Castillo |
| 4,660,240 | A | 4/1987 | Hutton et al. |
| 4,738,341 | A | 4/1988 | Asano |
| 4,854,308 | A * | 8/1989 | Drillio ............... A61F 5/0123 602/16 |
| 4,856,501 | A | 8/1989 | Castillo et al. |
| 4,991,571 | A | 2/1991 | Kausek |
| 4,993,127 | A | 2/1991 | Mechem et al. |
| 5,022,391 | A | 6/1991 | Weidenburner |
| 5,131,385 | A | 7/1992 | Kuehnegger et al. |
| 5,230,697 | A | 7/1993 | Castillo et al. |
| 5,288,286 | A | 2/1994 | Davis et al. |
| 5,288,287 | A * | 2/1994 | Castillo ............... A61F 5/0123 602/16 |
| D346,028 | S | 4/1994 | Lengyel |
| 5,311,972 | A | 5/1994 | Plath |
| 5,336,161 | A | 8/1994 | Lengyel |
| D357,070 | S | 4/1995 | Castillo |
| 5,415,625 | A | 5/1995 | Cassford et al. |
| D359,710 | S | 6/1995 | Chinni et al. |
| 5,458,565 | A | 10/1995 | Tillinghast, III et al. |
| D372,983 | S | 8/1996 | Nebolon |
| 5,571,078 | A | 11/1996 | Malewicz |
| 5,577,998 | A | 11/1996 | Johnson, Jr. et al. |
| 5,586,970 | A | 12/1996 | Morris et al. |
| 5,743,865 | A | 4/1998 | Townsend |
| 5,766,140 | A | 6/1998 | Tillinghast, III et al. |
| 5,782,780 | A | 7/1998 | Mason et al. |
| 5,807,294 | A | 9/1998 | Cawley et al. |
| 5,891,071 | A | 4/1999 | Stearns et al. |
| 6,056,713 | A | 5/2000 | Hayashi |
| 6,155,998 | A | 12/2000 | Gilmour |
| D435,807 | S | 1/2001 | Anscher |
| RE37,297 | E | 7/2001 | Smith, III |
| 6,290,664 | B1 | 9/2001 | Nauert |
| 6,361,515 | B1 | 3/2002 | Gilmour |
| 6,425,166 | B1 | 7/2002 | Seligman et al. |
| 6,461,318 | B2 | 10/2002 | Freeman et al. |
| 6,623,439 | B2 | 9/2003 | Nelson et al. |
| 6,687,963 | B1 | 2/2004 | Chang |
| 6,689,080 | B2 | 2/2004 | Castillo |
| 6,702,770 | B2 | 3/2004 | Bremer et al. |
| 6,719,713 | B2 | 4/2004 | Mason |
| 6,740,054 | B2 | 5/2004 | Stearns |
| 6,793,641 | B2 | 9/2004 | Freeman et al. |
| 6,796,952 | B2 | 9/2004 | Nelson et al. |
| 6,866,646 | B2 | 3/2005 | Hopkins et al. |
| 6,875,187 | B2 | 4/2005 | Castillo |
| 6,878,126 | B2 | 4/2005 | Nelson et al. |
| 6,890,314 | B2 | 5/2005 | Seligman |
| 6,936,019 | B2 | 8/2005 | Mason |
| 6,962,571 | B2 | 11/2005 | Castillo |
| 6,978,523 | B2 | 12/2005 | Downing et al. |
| 7,045,694 | B2 | 5/2006 | Yasunori |
| 7,059,329 | B2 | 6/2006 | Mason et al. |
| 7,120,982 | B2 | 10/2006 | Downing et al. |
| 7,125,392 | B2 | 10/2006 | Scott |
| 7,201,728 | B2 | 4/2007 | Sterling |
| 7,204,819 | B2 | 4/2007 | Berger |
| 7,207,960 | B2 | 4/2007 | Kenney |
| 7,231,698 | B2 | 6/2007 | Downing et al. |
| 7,261,700 | B2 | 8/2007 | Verkade |
| 7,285,103 | B2 | 10/2007 | Nathanson |
| 7,311,687 | B2 | 12/2007 | Hoffmeier et al. |
| D565,461 | S | 4/2008 | Johnson et al. |
| 7,426,773 | B2 | 9/2008 | Downing et al. |
| 7,431,708 | B2 | 10/2008 | Sreeramagiri |
| D581,315 | S | 11/2008 | Paris et al. |
| 7,462,160 | B2 | 12/2008 | Nobbe et al. |
| 7,479,122 | B2 | 1/2009 | Ceriani et al. |
| 7,534,219 | B2 | 5/2009 | Stearns |
| 7,562,422 | B2 | 7/2009 | D'Addario et al. |
| 7,601,131 | B2 | 10/2009 | Gilmour |
| 7,608,051 | B1 | 10/2009 | Nace |
| 7,749,183 | B2 | 7/2010 | Ingimundarson et al. |
| D627,073 | S | 11/2010 | Nace |
| 7,918,812 | B2 | 4/2011 | Knecht |
| 7,935,068 | B2 | 5/2011 | Einarsson |
| D647,622 | S | 10/2011 | Lee et al. |
| 8,043,243 | B2 | 10/2011 | Nathanson et al. |
| 8,048,013 | B2 | 11/2011 | Ingimundarson et al. |
| 2002/0013544 | A1 | 1/2002 | Stearns |
| 2002/0103449 | A1 | 8/2002 | Freeman et al. |
| 2002/0107464 | A1 | 8/2002 | Castillo |
| 2003/0045822 | A1 | 3/2003 | Nelson et al. |
| 2003/0045823 | A1 | 3/2003 | Nelson et al. |
| 2003/0144620 | A1 | 7/2003 | Sieller et al. |
| 2004/0097859 | A1 | 5/2004 | Stearns |
| 2004/0133139 | A1 | 7/2004 | Nelson et al. |
| 2004/0204667 | A2 | 10/2004 | Nelson et al. |
| 2006/0004311 | A1 | 1/2006 | Hargrave et al. |
| 2006/0084899 | A1 | 4/2006 | Verkade et al. |
| 2006/0129075 | A1 | 6/2006 | Scheinberg et al. |
| 2006/0135901 | A1 | 6/2006 | Ingimundarson et al. |
| 2006/0162135 | A1 | 7/2006 | Howell et al. |
| 2006/0167394 | A1 | 7/2006 | Ceriani et al. |
| 2006/0230583 | A1 | 10/2006 | Chen |
| 2007/0244419 | A1 | 10/2007 | Mason et al. |
| 2008/0195013 | A1 | 8/2008 | Ingimundarson et al. |
| 2008/0195014 | A1 | 8/2008 | Ingimundarson et al. |
| 2008/0195015 | A1 | 8/2008 | Ingimundarson et al. |
| 2008/0208095 | A1 | 8/2008 | Kazmierczak et al. |
| 2008/0237250 | A1 | 10/2008 | Swansey |
| 2009/0070969 | A1 | 3/2009 | Fildan et al. |
| 2009/0124948 | A1 | 5/2009 | Ingimundarson et al. |
| 2009/0287127 | A1 | 11/2009 | Hu et al. |
| 2012/0046584 | A1 | 2/2012 | Maloney |
| 2013/0296759 | A1 | 11/2013 | Maloney |

FOREIGN PATENT DOCUMENTS

| | | |
|---|---|---|
| WO | 2008/061300 A1 | 5/2008 |
| WO | 2010/088716 A1 | 8/2010 |

OTHER PUBLICATIONS

Product Information Sheet, "BREG, New! Fusion XT with AirTech Innovation", Orthofix Sports Medicine, obtained prior to Aug. 20, 2010, 1 page.

Product Information Sheet, "CTi OTS", obtained prior to Aug. 20, 2010, 1 page. Retrieved at www.ossur.com.

Product Information Sheet, "Paradigm Custom", obtained prior to Aug. 20, 2010, 1 page. Retrieved at www.ossur.com.

Product Information Sheet, "CTi Custom (color)", obtained prior to Aug. 20, 2010, 1 page. Retrieved at www.ossur.com.

Product Information Sheet, "The Total Support System", obtained prior to Aug. 20, 2010, 1 page. Retrieved at www.ossur.com.

International Search Report and Written Opinion from Corresponding PCT Application No. PCT/US2011/048228, dated Jun. 19, 2012.

\* cited by examiner

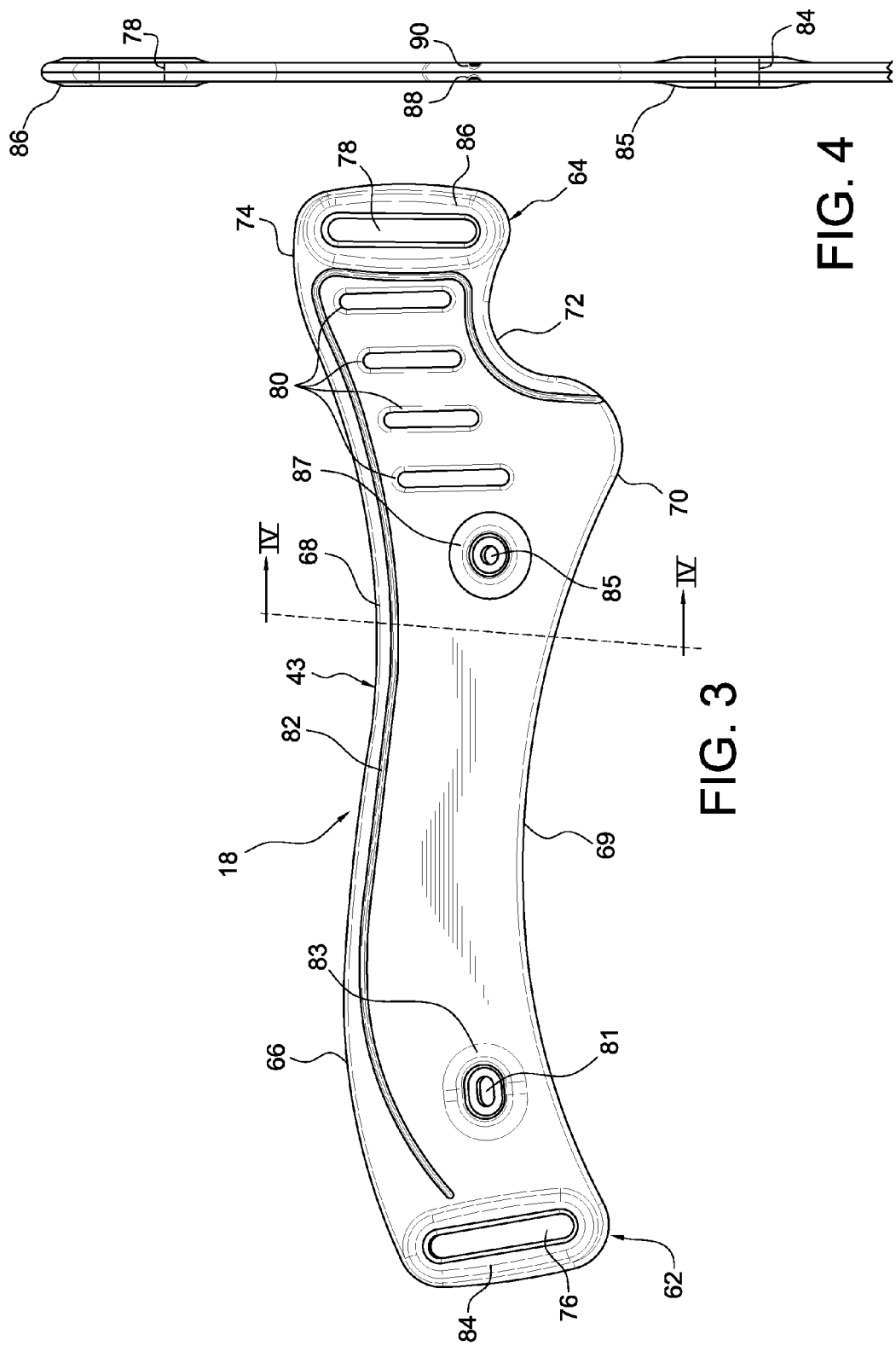

CONFIGURABLE SUBSHELL COMPONENTS IN ORTHOPEDIC DEVICES

CROSS-REFERENCE TO RELATED APPLICATIONS

This application is a continuation of U.S. application Ser. No. 13/212,382 filed Aug. 18, 2011, which claims the benefit of priority of U.S. provisional application Nos. 61/515,502, filed on Aug. 5, 2011, 61/375,380, filed on Aug. 20, 2010, and 61/375,392, filed on Aug. 20, 2010. The entirety of the disclosures of these provisional applications is incorporated herein.

FIELD OF THE DISCLOSURE

This disclosure generally relates to orthopedic devices, and particularly to configurable subshell components in combination with rigid or semi-rigid frame elements in orthopedic devices.

BACKGROUND

Orthopedic braces comprise a broad range of structures and devices used for supporting or stabilizing a joint when worn on the body of a user. Orthopedic braces may serve in either preventative or remedial roles. In the preventative role, the brace can provide additional support, stability and protection to a healthy joint so as to prevent or minimize injury to the joint due to undue stress. On the other hand, in the remedial role, the brace can support and strengthen a weakened joint due to injury or infirmity, and thereby reinforce the joint to prevent further injury, or correct or assist the infirmity.

Typically, orthopedic braces include a frame that comprises at least one support member. When there are multiple support members, the brace may include rotational hinges that assist and control movement of the limb. Suitable straps may be used to maintain the brace on the limb, and other features such as pads may be used to relieve pressure of the brace on the limb and surrounding areas.

A predominant type of orthopedic brace is a knee brace. Knee braces are used to stabilize the knee by preventing excessive movement of the knee, or to facilitate movement of the knee. Many braces comprise a frame and have hinges located on at least one of the lateral and medial sides of the knee joint. Straps are used to secure the brace to the leg or knee. An injured knee can be fit with an "off the shelf" brace or a "custom-fit" brace, with the selection of the type of brace depending on the size and shape of an individual's leg.

Many knee braces are designed to reduce knee instability following an injury, fatigue or to treat impairment of the knee, particularly if the knee has damaged ligaments. Braces may be recommended for walking, skiing, running, twisting, pivoting, or jumping activities. In addition to providing increased stability to the knee, braces may also decrease the risk of injuring the knee or leg, or provide corrective assistance to the knee.

In order to maximize its supportive, protective and comfort aspects, it is desirable that a knee brace securely and precisely fit the leg of the wearer. While custom-fit braces are made to closely conform to the exact geometry of a leg of a wearer, it is common for the geometry of the leg to change over time thereby requiring even a custom-fit to be able to accommodate a variety of geometries of the leg. As for off-the-shelf braces, these braces must be configurable to generally accommodate a variety of leg geometries irrespective of the particular geometry of a leg.

In recognizing the need for effective knee braces, various knee braces have been introduced into the marketplace. Such knee braces, however, have generally comprised relatively heavy, bulky apparatuses that fail to provide ventilation and evenly distribute pressure from the brace on the leg of the wearer. Moreover, many contemporary braces are deficient in that the braces are constructed in a manner that do not consistently provide or lack adjustment features for forming a firm, comfortable and secure interface between the leg and knee of the wearer and the brace. As a result of these drawbacks, many knee braces detract from the user's endeavor.

The features of the embodiments described herein are provided in recognition of the need for orthopedic braces and components for use therewith that are adjustable in both custom-fit and off-the-shelf braces so as to achieve superior functional performance characteristics while being comfortable to the wearer when worn. This recognition is realized with the invention described hereinafter.

SUMMARY

In an embodiment of an orthopedic device according to the invention, the device includes a rigid frame having a peripheral contour and first and second side portions, in which the frame is configured to conform to at least a portion of anatomy of a wearer. The device further includes a flexible subshell secured to the frame, and having a first end extending laterally beyond the first side portion so as to flex relative to the first frame side portion. The subshell has a contoured edge extending beyond the peripheral contour so as to flex relative to the frame peripheral contour. The subshell may be mounted along an interior surface of the frame. A strap has a first end secured to the first subshell end and a second end connected to the second frame side portion.

The subshell may have a second end flexibly extending beyond the second frame side portion, and the strap is secured to the second subshell end wherein tensioning of the strap draws the first and second subshell ends toward one another and away from the frame.

In a variation of the subshell, the subshell may have a living hinge spaced inwardly from the contoured edge and permits flexing of the contoured edge relative to the frame peripheral contour. The living hinge is defined at least in part by an elongate groove generally defined by the outline of the contoured edge. In another variation of the subshell, the subshell defines a living hinge spaced inwardly from the contoured edge extending along a upper segment of a length of the subshell and further extends generally downwardly toward a lower segment of the subshell length at the first subshell end.

The subshell end may define a slot generally normal to the length of the subshell, and the living hinge may be defined at least in part by an elongate groove generally defined by the outline of the contoured edge and runs along the slot. In a variation, the subshell may have a series of openings generally parallel to the slot.

The frame may define a plurality of locating holes, and the subshell can be adjustably mounted at the plurality of locating holes so as to adjust the subshell relative to the height of the frame.

In a variation of the frame, the frame defines at least one anchoring member extending from an interior surface, and the subshell defines at least one eyelet having a retaining member extending therein. The at least one eyelet is configured for receiving the at least one anchoring member and the retaining member arranged for engaging the at least one anchoring member in the eyelet.

Various embodiments of a tibial subshell assembly are disclosed herein including certain tibial subshells connected to different strapping systems for distributing pressure over the tibia of the wearer.

An embodiment of a leg wrap is described herein in combination with a brace frame wherein a portion of the leg wrap is adjacent to a rigid or semi-rigid brace frame. The leg wrap extends about the entirety of the circumference of the wearer's leg.

In another embodiment, a coupling device for an orthopedic brace includes a brace frame having an anchoring member protruding therefrom, and a subshell or retention member connected to the brace frame. The subshell or retention member has a locking element defining a receiving opening arranged to receive the anchoring member and an engaging opening having a width less than the receiving opening, and arranged to engage the anchoring member depending from the receiving opening. The subshell or retention member also has a retaining member extending into the engaging opening. The retaining member flexibly depends from the subshell or retention member such that when the receiving opening receives the anchoring member, the retaining member deflects away from the receiving opening, wherein when the anchoring member is moved to the engaging opening, the retaining member retains the anchoring member in place.

According to a variation, the anchoring member may be adjustable relative to interior and exterior sides of the brace frame. Further, the brace frame may include recessed portions to accommodate a portion of the anchoring member.

BRIEF DESCRIPTION OF THE DRAWINGS

The orthopedic device is described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein.

FIG. 3 is a plan view showing an embodiment of an upper subshell in the knee brace of FIG. 1.

FIG. 4 is an enlarged sectional elevational view showing a section IV-IV of the subshell depicted in FIG. 3.

DETAILED DESCRIPTION OF VARIOUS EMBODIMENTS

A. Overview

Figure 1:
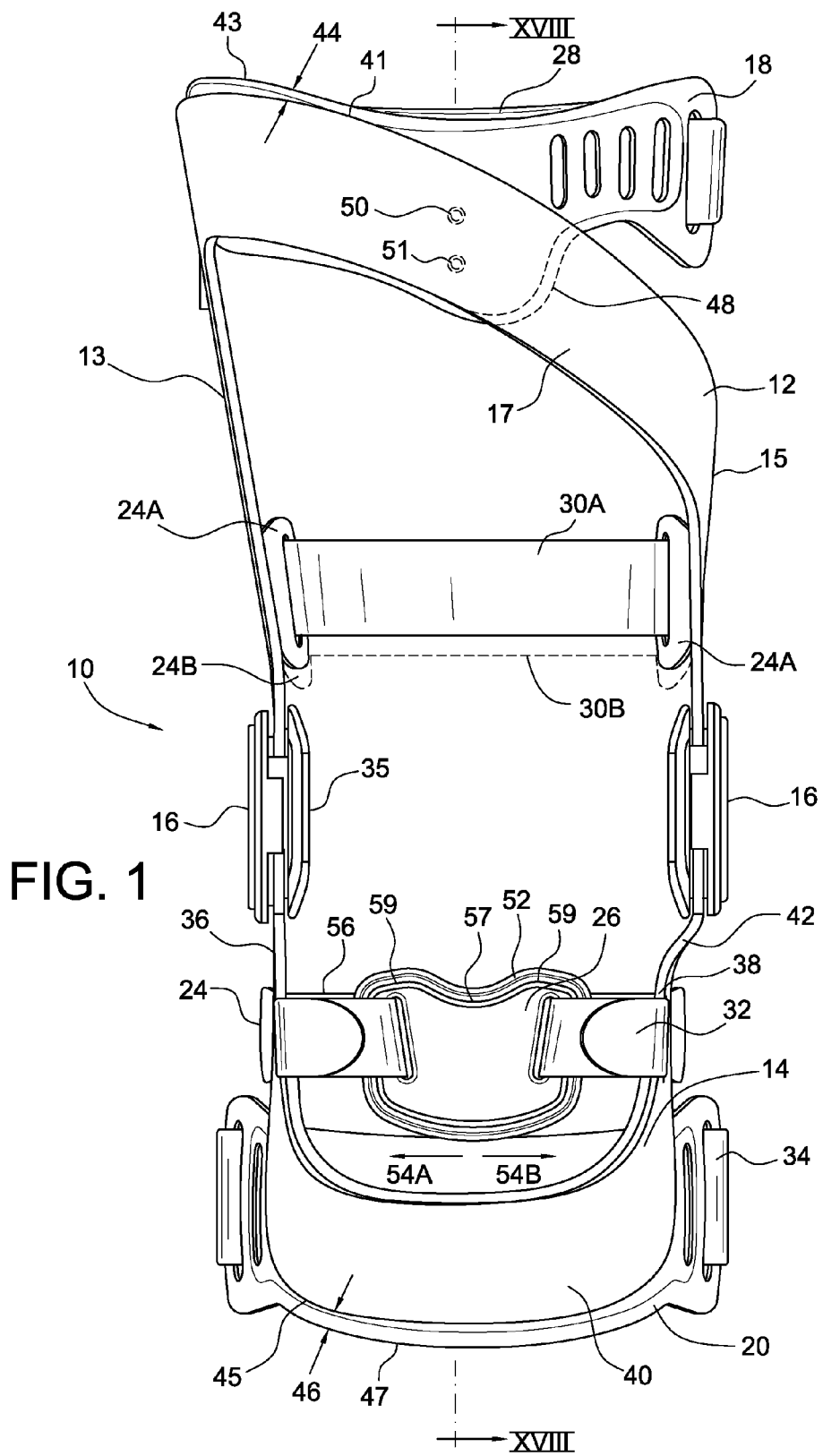
FIG. 1 is an elevational view showing an embodiment of an orthopedic device in the form of a knee brace.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Definitions

For ease of understanding the disclosed embodiments of an orthopedic device, the anterior and posterior portions of the orthopedic device are described independently. It will be recognized that the anterior and posterior portions of the orthopedic device function together to support and stabilize anatomical portions of the wearer of the device.

For further ease of understanding the embodiments of an orthopedic device as disclosed herein, a description of a few terms is necessary. As used herein, the term "proximal" has its ordinary meaning and refers to a location situated next to or near the point of attachment or origin or a central point, or located toward the center of the body. Likewise, the term "distal" has its ordinary meaning and refers to a location that is situated away from the point of attachment or origin or a central point, or located away from the center of the body. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," "compliant," and "resilient" may be used herein to distinguish characteristics of portions of certain features of the orthopedic device. The term "rigid" is intended to denote that an element of the device is generally devoid of flexibility. Within the context of frame or support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied.

The term "compliant" is used to qualify such flexible features as generally conforming to the shape of another object when placed in contact therewith, via any suitable natural or applied forces, such as gravitational forces, or forces applied by external mechanisms, for example, strap mechanisms. The term "resilient" is used to qualify such flexible features as generally returning to an initial general shape without permanent deformation. As for the term "semi-rigid," this term is used to connote properties of support members or shells that provide support and are free-standing; however such support members or shells may have some degree of flexibility or resiliency.

C. Various Embodiments of the Orthopedic Device and Components for Use Therewith FIG. 1 illustrates an orthopedic device in the exemplary form of a knee brace 10 having configurable subshell components in combination with rigid frame elements. The knee brace 10 includes an upper frame element 12 and a lower frame element 14 connected by lateral and medial hinges 16 having condyle pads 35. Preferably, the upper and lower frame elements are either rigid or semi-rigid. As an example, the frame elements may be formed from aluminum and may be malleable from a cold forming treatment so as to allow for easy customization of the frame elements to a particular leg shape. Other exemplary materials that may be used for constructing the frame include metals such as titanium, and steel, thermoset resin composite systems including glass or carbon fibers, and thermoplastics that have been rendered rigid by way of material composition and geometry of the frame members.

According to this embodiment, the upper frame element 12 is substantially rigid and is adapted to extend along portions of the lateral and medial sides of a leg and about the anterior portion of the thigh. Specifically, the upper frame element 12 includes a lateral upright section 13, a medial upright section 15, and a curved section 17 extending between the upper end portions of the lateral and medial uprights 13, 15. According to this embodiment, the curved section 17 spirals between the lateral and medial uprights 13, 15 since the medial upright 15 has a shorter length than the lateral upright 13. The curved section is "curved" in the sense that it is adapted to curve about at least part of the anterior circumference of the wearer's leg.

The lower frame element 14 is substantially rigid and is adapted to extend along portions of the lateral and medial sides of the leg and about the anterior portion of the tibia of the lower leg. The lower frame element 14 includes a lateral upright 36, a medial indented member 42 located at a medial side upper end, a medial upright 38, and an anterior curved section 40 extending between the lower end portions of the lateral and medial uprights 36, 38.

The illustrated example of the upper and lower frame elements shows each frame element as being formed integrally. However, those of skill in the art will appreciate that these components could be formed separately and be secured to one another with welds, fastening members, etc. Moreover, while the upper and lower frame elements are depicted and described as having a particular configuration, the configuration may be modified to extend along different portions of the leg (i.e., posterior) and may have different length relationships (i.e., lateral upright versus medial upright).

A flexible upper subshell 18 is mounted onto an interior surface of the upper frame element 12. A strap 28 connects to opposed sides of the subshell and extends about the posterior side of the knee brace 10. The upper subshell 18 extends proximate to a segment of the curved section 17, such that a medial portion 48 of the upper subshell 18 terminates prior to the medial upright 15. A flexible lower subshell 20 is mounted onto an interior surface of a lower frame element 14, and a strap 34 connects to opposed sides of the lower subshell 20. Because the upper and lower subshells 18, 20 are flexible, when the straps 28, 24 are tensioned, opposed end portions of the subshells connecting to the straps are drawn toward one another.

Both the upper and lower subshells 18, 20 are sized and configured so that a portion of peripheral edges of the subshells extends beyond the peripheral edges of the upper and lower frame elements 12, 14. For example, an upper peripheral edge 43 of the upper subshell 18 is spaced by a distance 44 from an upper peripheral edge 41 of the upper frame element 12. In another example, a lower peripheral edge 47 of the lower subshell 20 extends a distance 46 beyond the lower peripheral edge 45 of the lower frame element 20. Because the subshells are flexible, the portions of the subshells extending beyond the peripheral edges of the frame portion are arranged for flexing relative to the rigid frame elements. Other examples, such as end portions of the subshells arranged to receive straps, will be discussed in greater detail in connection with more specific examples of the upper and lower subshells.

The subshells are adjustably mounted to a variety of locations on the frame elements. For example, the upper subshell 18 can be mounted at one of the two locating apertures 50, 51, extending from the interior surface of the upper frame element which enables for adjustment of the distance 44 between the upper peripheral edge 43 of the upper subshell 18 and the upper peripheral edge 41 of the upper frame element 12.

The knee brace 10 includes D-rings 24, as will be explained in greater detail in connection with FIGS. 13 and 14, which are arranged to carry posterior straps 30, 56 between the lateral and medial sides of the knee brace. In addition, the D-rings may be mounted at a plurality of locations along an interior surface of the upper and lower frame elements, as exemplified with D-rings 24A and strap 30A at a first location, and D-rings 24B and strap 30B at a second location along the length of the upper frame element.

The knee brace 10 also comprises a tibial subshell 26 that is adjustably mounted on a strap 32 secured between the lower lateral and medial uprights 36, 38. The tibial subshell 26 is preferably constructed from a flexible polymeric material but sufficiently rigid to provide support, and arranged to provide support to the tibia of the wearer. The tibial subshell 26 includes a pad 52 mounted on its interior surface adjacent the wearer. Further, the tibial subshell 26 defines an upper periphery having a recessed portion 57 arranged to correspond to the tibia with peak portions 59 located on opposed sides of the recessed portion 57 so as to better conform to the anatomy of the lower leg.

The tibial subshell is adjustable so that its location can be adjusted relative to the preferred location for an individual wearer of the brace. The center of the brace may not necessarily align with the tibia of the wearer. This configuration is advantageous in that the wearer can adjust the location of the subshell so that it can always or mostly be centered on the tibia of the wearer.

Figures 2A, 2B:
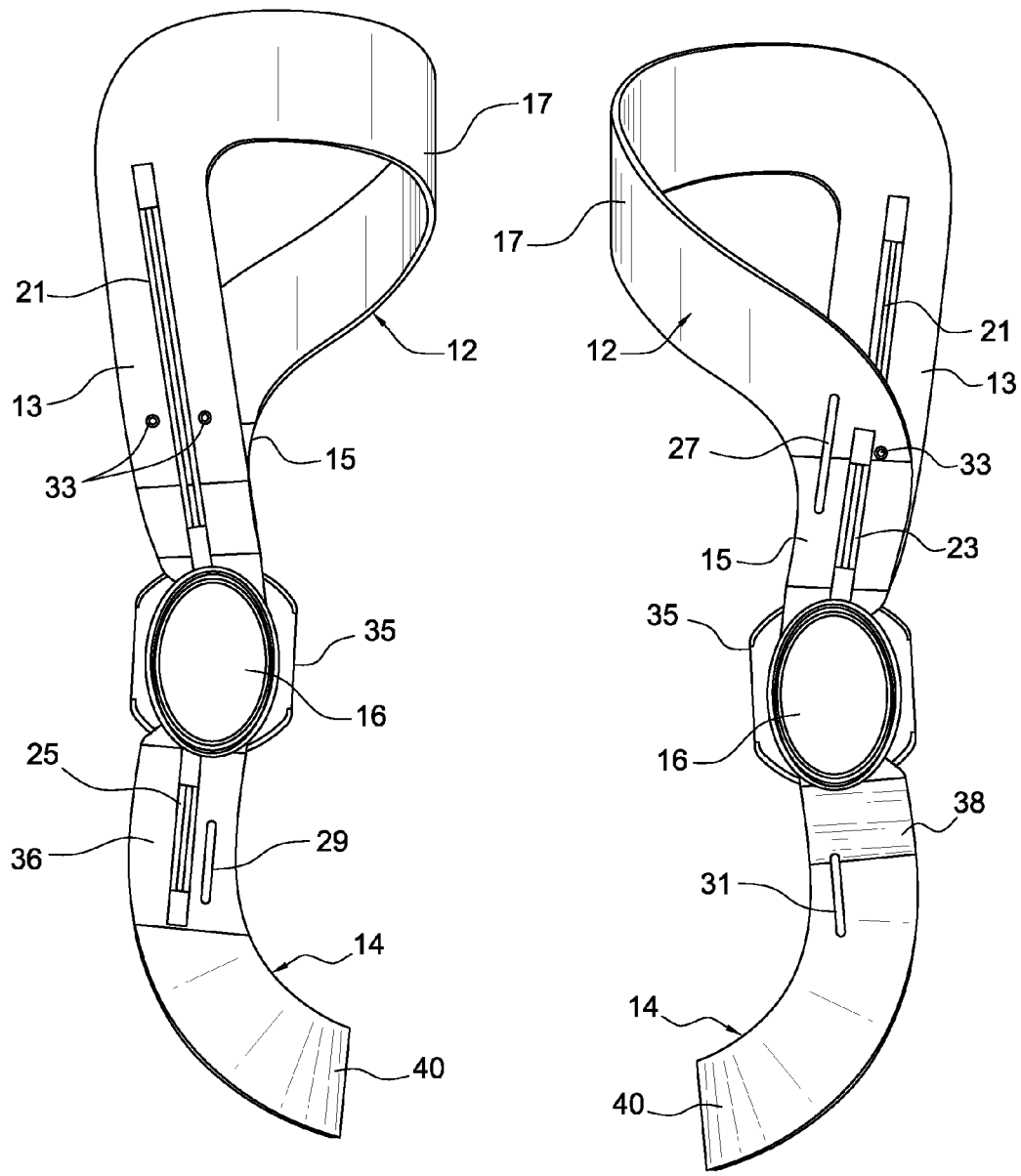
FIGS. 2A and 2B are elevational views showing lateral and medial sides of a variation of the knee brace of FIG. 1.

FIGS. 2A and 2B illustrate a variation of the upper and lower frame elements 14 secured to one another via lateral and medial hinges 16. The upper frame element 14 defines strengthening ribs 21, 23 formed on lateral and medial sides of the lateral and medial uprights 13, 15. The strengthening ribs preferably protrude from the outside of the lateral and medial uprights, and are generally parallel with the length of the lateral and medial uprights, and centrally located within the width of the uprights. The lower lateral upright 36 forms a strengthening rib 25, whereas the lower medial upright 38 lacks a strengthening rib.

The strengthening ribs provide additional strength to the upper and lower frame elements, as considered necessary when the frame elements are inherently less rigid; for example, in aluminum based frame elements which are generally lightweight and cold or heat moldable. The strengthening ribs may be located along various portions of the upper and lower frame elements, and the configuration is not limited to the depiction in FIGS. 2A and 2B.

The upper medial upright 15 defines a slot 27 for receiving the strap 30A, and the upper lateral upright 13 defines apertures 33 for securing attachments, for example b-rings, for connecting to the strap 30A on the upper lateral upright 13. The slots may be replaced by the apertures for securing attachments, or provided in combination with the slots. The lower lateral and medial uprights 36, 38 likewise define slots 29, 31 for receiving the strap 32.

Turning to FIGS. 3 and 4, an embodiment of the upper subshell 18 is depicted in greater detail. The upper subshell 18 defines lateral and medial portions 62, 64, whereby each portion defines a slot 76, 78, respectively, for receiving a strap (as in strap 28 in FIG. 1) and generally perpendicular to the length of the subshell. Both the lateral and medial portions 62, 64, are arranged to extend beyond the periphery of the upper frame element generally toward a posterior direction of the brace. Particularly, the slots 76, 78 are configured so that they can bend upon tensioning of the strap and flex relative to the upper frame element.

Each of the slots 76, 78 defines a reinforced edge 84, 86, respectively, raised from the subshell thickness and arranged to reinforce the subshell from the strap. Moreover, the medial portion 64 defines a plurality of elongate openings 80 provided in part to ventilate the subshell as well as facilitate bending of the subshell relative to the frame element.

The upper subshell 18 defines a periphery that conforms, at least in part, to the contours of the upper frame element, as shown in FIG. 1. For example, the upper subshell 18 defines a lateral upper curved section 66 corresponding to the peripheral contour of the lateral side of the upper frame element, as well as a recessed upper curved section 68 corresponding in part to the downwardly spiral of the curved segment of the upper frame element. The upper subshell 18 also defines a lower curved section 69 generally conforming to a portion of the contour of the upper frame element.

In view of the downward curvature of the upper frame element, and in order to maintain the strap as extending generally laterally or horizontally across a thigh of the wearer, the upper subshell 18 includes an upwardly medial curved section 74 extending from the recessed curved section 68. Additionally, a downward extension 70 terminates the lower curved section 69, whereas an upward extension 72 depends from the downward extension 70 and generally conforms to the upwardly medial curved section 74.

The upper subshell 18 defines an elongate flexure feature or living hinge 82 spaced downwardly from the upper peripheral edge 43, and generally corresponding to the lateral upper curved section 66, the recessed curved section 68, and the contours of the medial portion 64 of the upper subshell 18. The flexure feature 82 is defined by its contour as well as interior and exterior surface grooves 88, 90 formed on the interior and exterior surfaces of the subshell.

The flexure feature 82 is preferably aligned along the peripheral edge of the frame element so the upper peripheral edge 43 of the upper subshell can extend the distance away from the peripheral edge of the frame element. The flexure feature 82 assists the subshell to flex relative to the frame element in order to provide added relief to the wearer and minimize the frame element from cutting into or deeply indenting the leg of the wearer.

The upper subshell 18 forms lateral and medial side locating apertures 81, 85 having reinforced sections 83, 87, respectively, therearound. The locating aperture 81 forms an elongate slot permitting lateral or horizontal adjustment of the subshell relative to the upper frame element. As shown in FIG. 1, apertures 50, 51 at two successive height locations can receive fasteners, such as a binding nut, to engage the locating aperture 81 so as to adjust the location of the upper subshell relative to the frame element.

The adjustability of the subshell is particularly advantageous in order to provide a more customizable fit of the subshell relative to the frame elements. For example, with the upper subshell 18 fixedly secured (at one end) to the upper frame element 12, the curvature of the upper subshell 18 relative to the curved section 17 may be adjusted accordingly to the geometry of the thigh of the wearer of the brace.

Figure 5:
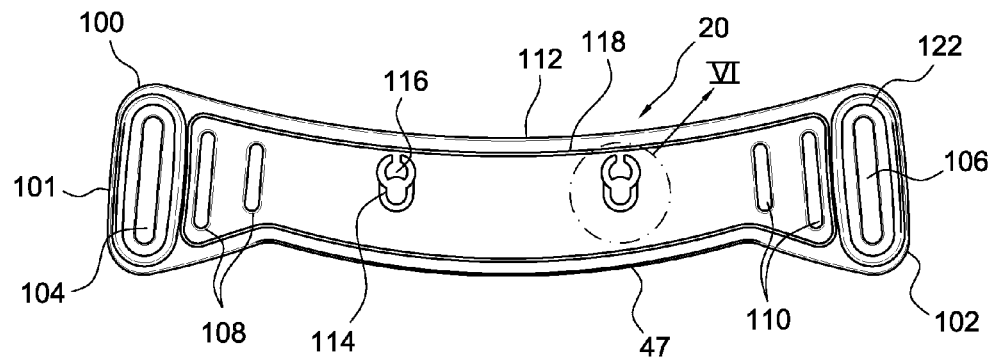
FIG. 5 is a plan view showing an embodiment of the lower subshell in the knee brace of FIG. 1.
Figure 6:
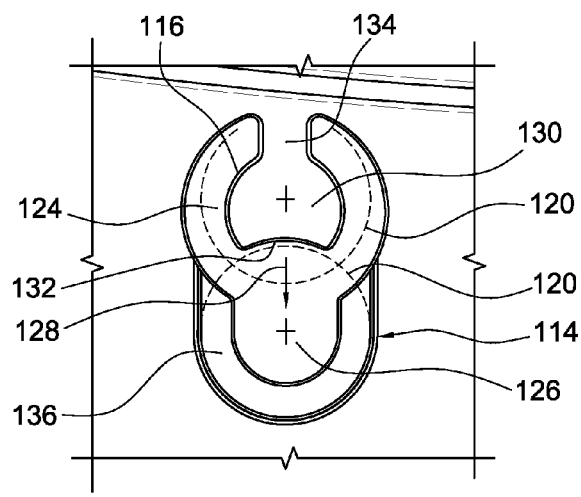
FIG. 6 is an enlarged sectional view taken from FIG. 5.

FIGS. 5 and 6 depict an embodiment of the lower subshell 20. The lower subshell 20 defines lateral and medial portions 101, 102, whereby each portion defines a slot 104, 106, respectively, for receiving a strap (as in strap 34 in FIG. 1) and generally perpendicular to the length of the subshell. A reinforced edge 122 surrounds each of the slots 104, 106.

Both the lateral and medial portions 101, 102, are arranged to extend beyond the periphery of the upper frame element generally toward a posterior direction of the brace. Particularly, the slots 104, 106 are configured so that they can bend upon tensioning of the strap and flex relative to the upper frame element.

The lower subshell 20 defines upper and lower curved peripheral edges 112, 47, respectively, that correspond to the contours of the peripheral edges of the lower frame element, as in lower peripheral edge 45. As with the upper subshell, the lower subshell 20 includes a flexure feature or living hinge 118 formed by example from an elongate groove, as well as lateral and medial elongate openings 108, 110 formed generally parallel to the slots 104, 106 to provide ventilation and flexure for the lateral and medial portions 101, 102.

The lower subshell 20 defines a locking element 114 having a retaining member 116, and which is arranged to secure to an anchoring member 120 mounted along one of the frame elements. The anchoring members 120 may be fixedly secured to the frame uprights, or may be releasably securable to the frame uprights, such as by threadable engagement with the uprights, as shown in FIG. 14 with threads 155 formed along the anchoring member and received by corresponding threads of the frame upright. Preferably, as shown in FIG. 5, the lower subshell 20 defines a pair of locking elements 114 adapted to secure to the lower frame element.

Particularly, the locking element 114 defines a receiving opening 124 arranged to receive the anchoring member 120 and an elongate engaging opening 126 having a width less than the receiving opening 124 and depends from the receiving opening 124. The configuration of the receiving opening 124 relative to the engaging opening 126 permits inserts of the anchoring member 120 into the locking element 114 and retention of the anchoring member therewithin.

The retaining member 116 flexibly depends from the subshell 20 such that when the receiving opening 124 receives the anchoring member 120, and the retaining member 116 deflects away from the receiving opening 124, wherein when the anchoring member 120 is moved in direction 128 to the engaging opening 126 whereat the retaining member 116 retains the anchoring member 120 in place.

The retaining member 116 comprises an extension portion 134 depending from the subshell and extends into the receiving opening 124. A head portion 130 depends from the extension portion 134 into the receiving opening 124 and generally conforms to the shape of the receiving opening 124. An arcuate recessed portion 132 is formed along the head portion 134 and is adjacent to and borders the engaging opening 126. When the anchoring member 120 is located in the engaging opening 126, the recessed portion 132 is arranged to be flush against a peripheral edge of the anchoring member 120. The extension portion 134 permits flexure of the retaining member 116 out from the receiving opening 124.

The locking element 114 defines an insert region 136 generally alongside the engaging portion 126 and formed from a reduced thickness area of the subshell. The insert region 136 is arranged to receive portions of the anchoring member laterally adjacent to the engaging portion 126 so as to reduce extension of the anchoring member from the subshell.

Figure 7:
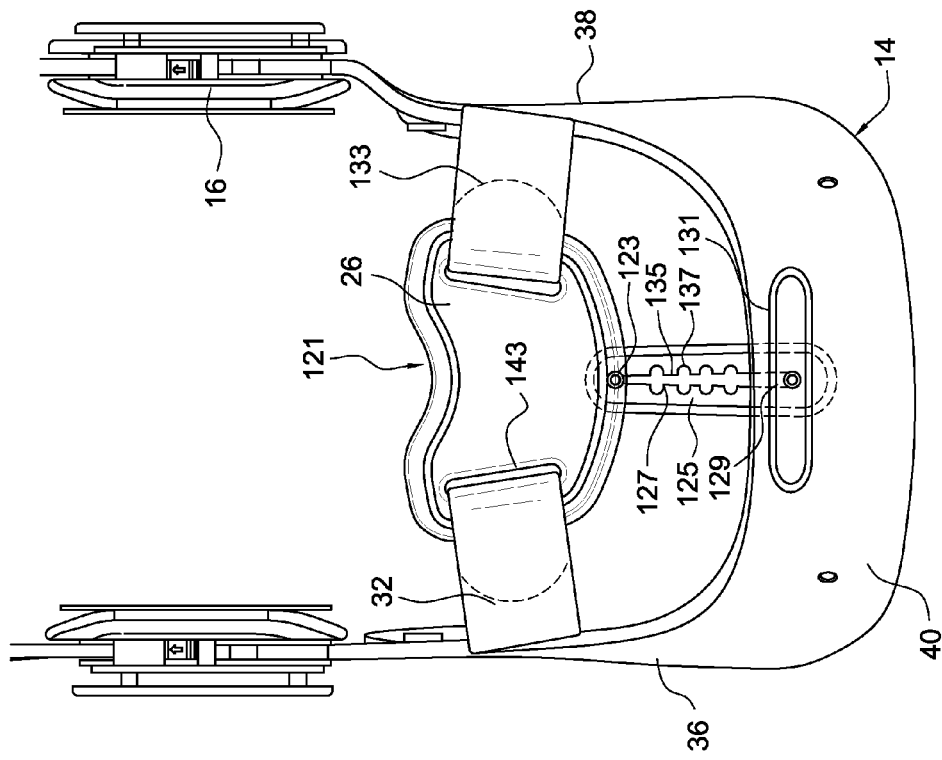
FIG. 7 is an elevational view of a variation of a tibial subshell assembly.

FIG. 7 depicts a variation of the tibial subshell 26 according to FIG. 1. In this variation, the tibial subshell assembly 111 includes the basic tibial subshell 26 which is incorporated with a liner 115 secured to a posterior or rear side of the lower frame element 14. A stem 117 bridges the portions of liner 115 adjacent the lower frame element 14 to the tibial subshell 26 and extends generally centrally from the anterior curved section 40. The tibial subshell 26 is preferably surrounded by the liner 115 by the border portion 119, and the rear portion of the tibial subshell is likewise covered by the liner 115. The front side of the tibial subshell 26 is preferably exposed and uncovered by the liner 115.

The tibial subshell 26 is connected to the lateral and medial uprights 36, 38 by the strap 32. In this embodiment, the strap 32 is secured under and over slots or other attachments to the lateral and medial uprights 36, 38. The strap is preferably inelastic so as to provide consistent posterior force on the tibia of the wearer when the strap 32 is tensioned.

The liner may be formed from a variety of different materials such as cushioning materials or combinations thereof. For example, the liner may be formed according to any of the embodiments described in U.S. patent application Ser. No. 12/774,882, filed on May 6, 2010, and incorporated herein by reference.

The stem allows for additional stability of the tibial subshell over the tibia of the wearer, and the extension of the liner allows for more cushioning over the tibia. In an alternative, the stem may be replaced by a strap which allows for height adjustment of the tibial subshell over the tibia, with a slot or other attachment means being provided on the anterior curved section.

Figure 8:
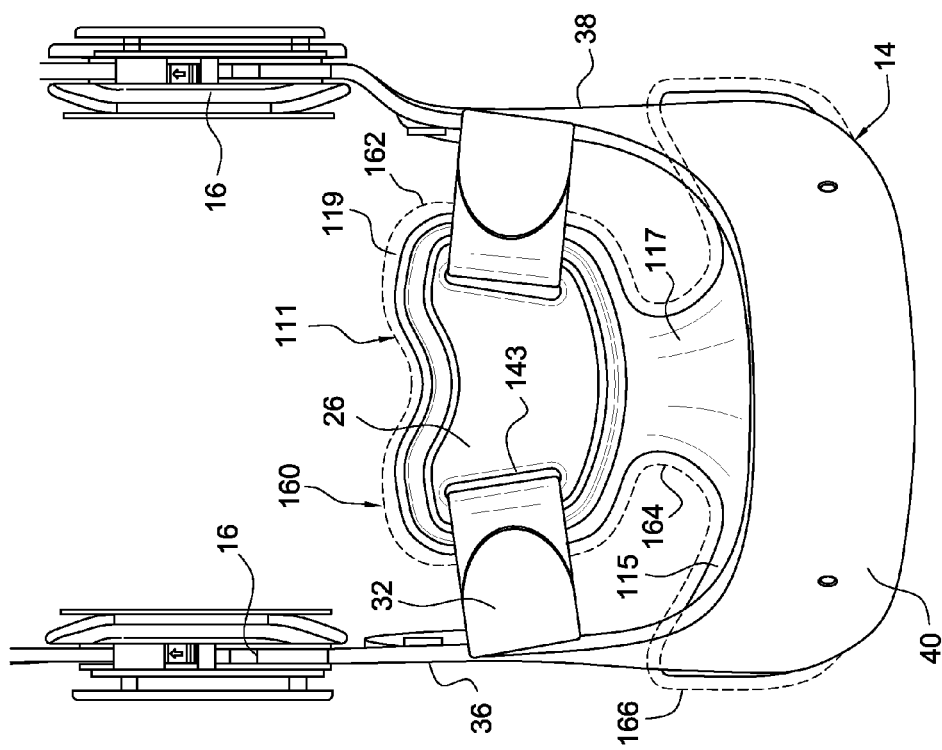
FIG. 8 is an elevational view of another variation of a tibial subshell assembly.

FIG. 8 shows another variation of the tibial subshell assembly 121 having the tibial subshell 26. In this variation, the tibial subshell 26 is pivotally connected to the anterior curved section 40 by a stem 125, and the tibial subshell 26 is pivotally connected to the stem 125 at the upper pivot device 123, so as to be adjustably positioned along the length of the stem 125 at the locking positions 127.

The upper pivot device 123 may be adjustably loosened so as to permit adjustment of the tibial subshell 26 at the various the locking positions 127. For example, the upper pivoting device 123 can be shaped so that turning it in one direction will allow the locking device to slide along a slot 135 formed along the stem 125, but upon turning in an opposite direction, the locking device 125 secures at apertures 127. Other configurations may be used such as ratcheting devices or other known systems available to the skilled artisan.

The stem 125 may be pivotally secured to the anterior curved section 40 at lower pivot point 129. In addition, the anterior curved section may include a slot 131 provided with or without the locking positions 137 on the stem 125. In the configuration wherein the slot is open without additional elements, the step can slide relative to the anterior curved section.

It will be noted that the stem may be selectively connected to the tibial subshell either at the upper or lower pivot points or the stem may be secured to the tibial subshell at fixed points.

In another embodiment, the tibial subshell may be formed integrally with the lower subshell. Taking FIG. 7 for instance, a tibial lower subshell combination 160 (denoted by the dashed lines for exemplary purposes) includes the tibia subshell 162, a stem 164 and a lower subshell 166, all of which are formed as a single piece.

The tibial lower subshell combination 160 defines strap slots 106 for receiving straps 32, as in any of the aforementioned embodiments, extending from opposed sides of the uprights which advantageously allows for different tensioning on either the lateral or medial sides of the tibia subshell 162. The lateral and medial side straps are particularly advantageous over know strap systems whereby a single strap is arranged to overlie that tibia subshell. In these known systems, there is a tendency for the strap to slip from the tibia subshell and come into direct contact with the leg of the wearer such that the tibia subshell is no longer pressed against the leg of the wearer.

According to any of the embodiments of the tibia subshell, it may be formed of a material, such as ELLASTOLLAN, that is sufficiently soft to allow for trimming of the subshell to the anatomy of the wearer. This is particularly advantageous in the field setting whereby a clinician can modify the subshell so as to obtain a more custom fit. Any of the subshells may be formed from such sufficiently soft materials to better enable customization of the brace to a particular wearer.

The straps 32 may secure to the lateral and medial uprights 36, 38 much in the manner in FIG. 7. In an alternative variation, as shown in FIG. 8, unlike in the variation of FIG. 7 wherein the straps are secured over the lateral and medial uprights, the straps are secured over and under the lateral and medial uprights. In yet another variation, the tibial subshell may be molded or fixedly secured to a strap secured at opposed ends to the lateral and medial uprights.

Figure 9:
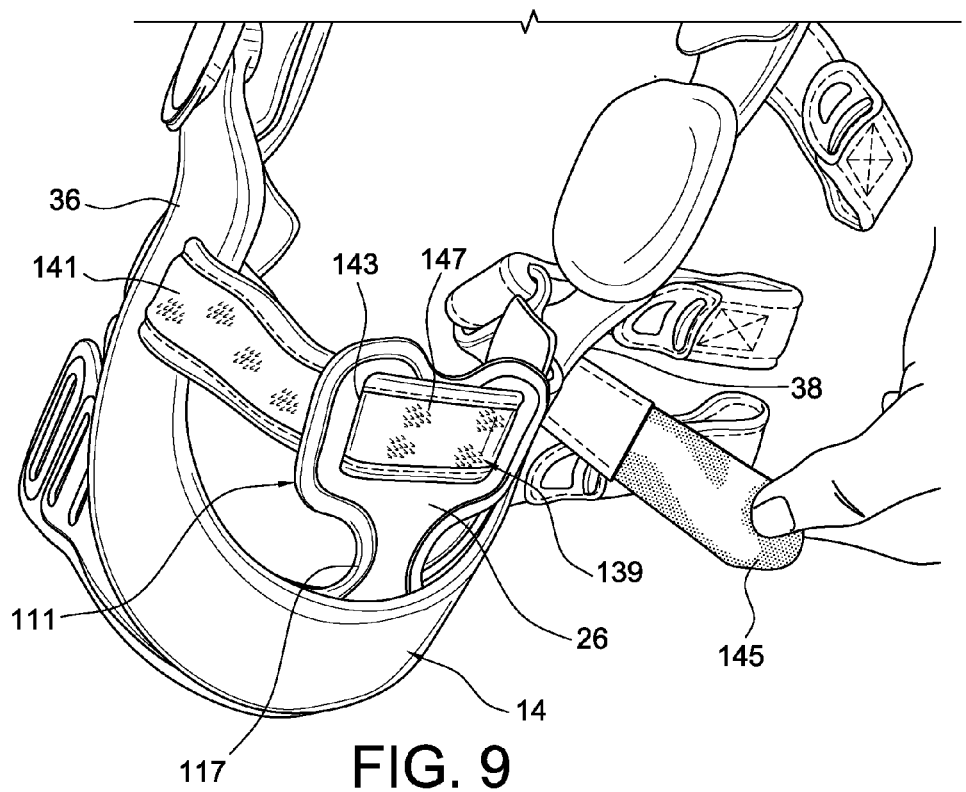
FIG. 9 is a perspective view of another variation of the tibial subshell assembly.

FIG. 9 illustrates a strap variation of the tibial subshell assembly 111 in FIG. 7. Specifically, a strap 139 has a first end 141 secured to the lateral upright 36. The strap 139 feeds through lateral and medial slots 143 formed by the tibial subshell 26 with a center portion 147 of the strap 139 extending over an anterior or exterior surface of the tibial subshell 26. The strap 139 secures to the medial upright 38, with a second end 145 of the strap 139 extending freely relative to the medial upright 38. The second end 145 carries hook material (or other suitable fastener), and is securable to the strap 139, including the center portion 147 exposed over the tibial subshell 26. Pressure is exerted over the tibial subshell 26 and is directed onto the tibia of the wearer, yet pressure is distributed over the wearer's tibia.

Figure 10:
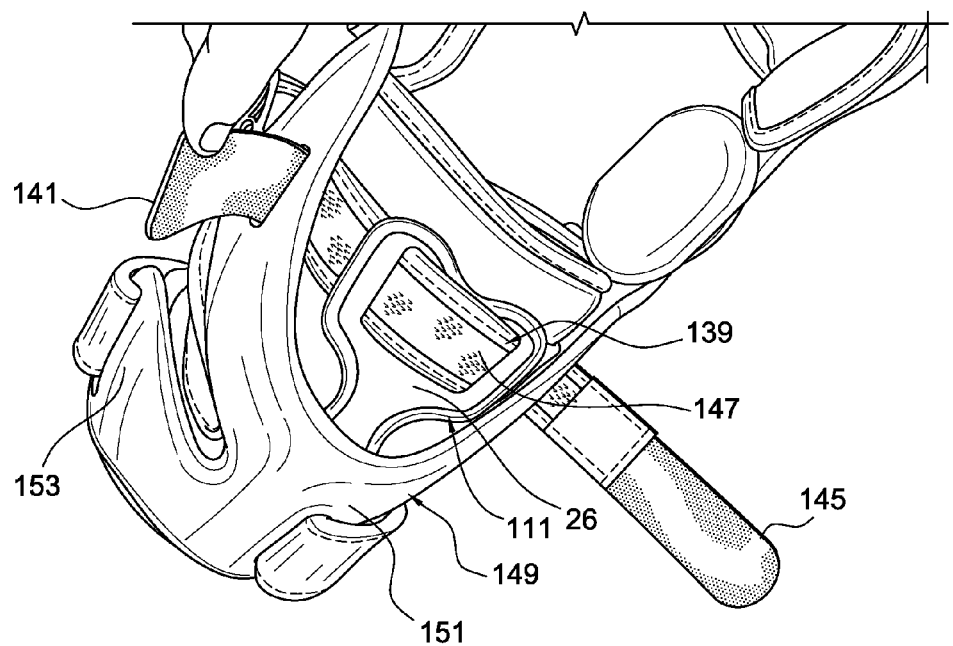
FIG. 10 is a perspective view of another variation of a tibial subshell assembly.

In FIG. 10, a variation of the tibial subshell assembly 111 of FIG. 9 is shown, wherein the strap 139 is secured to the tibial subshell 26 in a similar manner, however both the first and second ends 141 and 145 extend freely from the lateral and medial uprights, respectively, and are securable over either each other or the center portion 147 of the strap 139.

FIG. 10 also illustrates a different structure of the lower frame element 149. Specifically, the lower frame element 149 includes an anterior curved section 151 with a lateral arm 153 extending therefrom.

Figure 12:
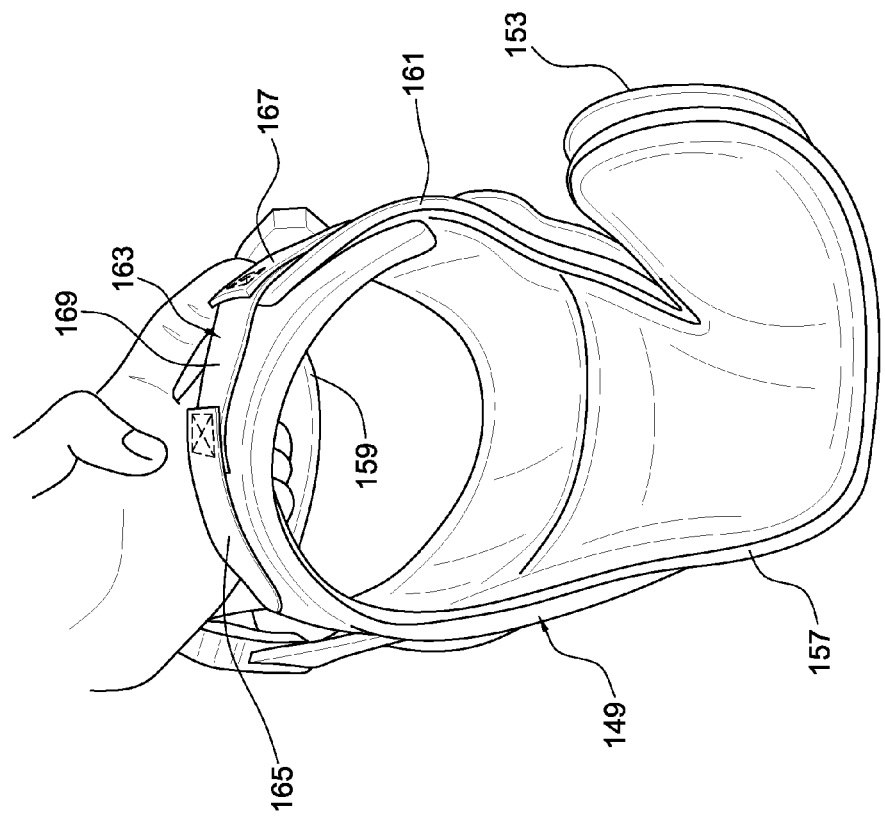
FIG. 12 is a perspective view of the lower leg wrap of FIG. 11 in a closed configuration.
Figure 11:
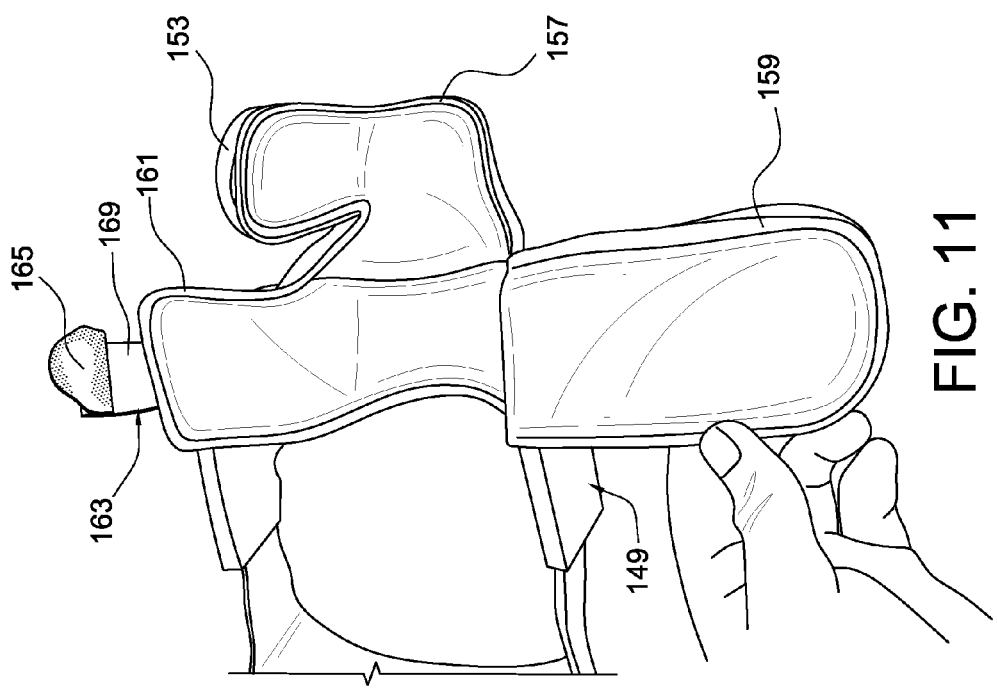
FIG. 11 is a perspective view of a lower leg wrap showing in an open configuration.

FIGS. 11 and 12 show a compliant anti-migration strap wrap 157 configured on the lower frame element 149. The wrap 157 defines a general shape of the lower frame element 149, and has opposed first and second sides 159, 161 proximate to the tibial subshell assembly that secure to one another without any corresponding rigid or semi-rigid structure located on the posterior side of the brace. The first side 159 has a longer length extending freely from the lower frame element 149, and wraps at least over the posterior leg of the wearer.

The second side 161 wraps over an exterior surface of the first side so that the wrap 157 circumferentially extends around the entirety of the lower leg of the wearer, with only the anterior portion of the wrap necessarily corresponding to rigid or semi-rigid structure. This is particularly advantageous in that the bony portions, such as the shin on the anterior side of the lower leg, have corresponding rigid or semi-rigid structure associated therewith, whereas the fleshy portion of the lower leg, such as the calf portion on the posterior side of the leg, has a substantially flexible material associated therewith allowing for muscles movement, flexibility and comfort.

A strap 163 secures to the exterior surface of both the first and second sides 159, 161 so as to securely couple them together. Preferably, the strap 163 includes first and second sides 165, 167 that have a fastener, such as hook material, that permit them to secure to the first and second wrap sides 159, 161. A center portion 169 of the strap 163 is located between the first and second sides 165, 167. The center portion 169 may be formed from a stretchable or flexible material so as to better accommodate movement of the posterior portion of the wearer's leg.

The wrap preferably includes a friction medium that engages the lower leg to prevent movement thereagainst. An example of a type of structure of the wrap can be a compliant spacer element found in U.S. patent application Ser. No. 12/774,882.

Figure 13:
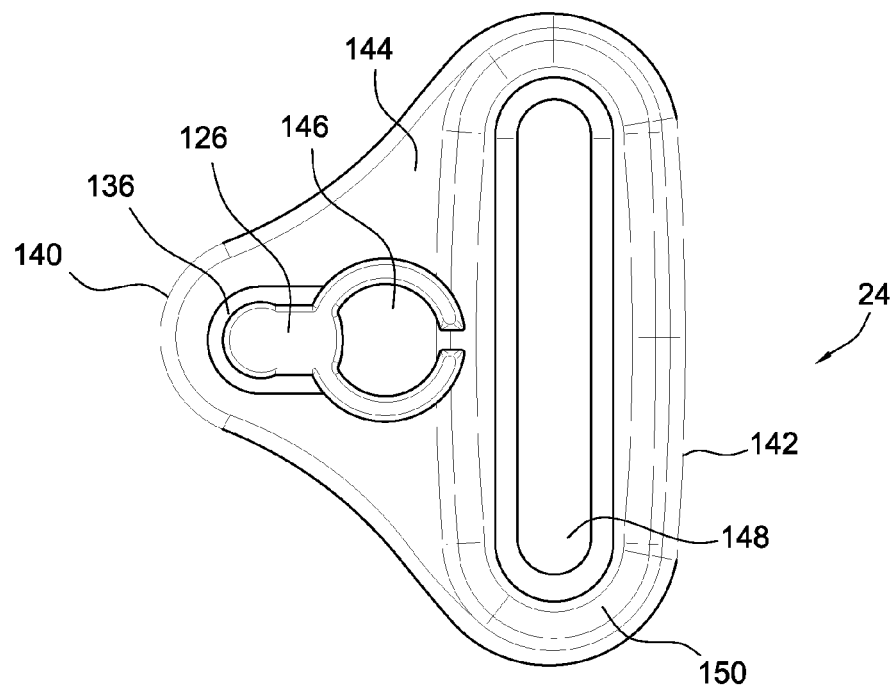
FIG. 13 is an embodiment of a D-ring for use in an orthopedic device.

As illustrated in FIG. 13, an embodiment of a subshell in the form of a D-ring or retention member 24 defines forward and rearward portions 140, 142. An elongate slot 148 is formed at the rearward portion 142 of the D-ring 24 and a reinforced edge 156 of types described in connection with the subshells is provided around the elongate slot 154. The D-ring 24 includes a locking element 146 constructed much in the same manner as the locking element 114. The D-ring 24 may be flexible so as to conform to the anatomy of a leg of the wearer, or the D-ring 24 may be rigid. Of note, the elongate slot 148 is generally perpendicular to the elongate engaging opening 126, which further allows for the anchoring member to be retained when a strap is inserted through the strap slot and tensioned.

The D-ring 24 has a body 144 with a thickness that is less than a reinforced area 146 surrounding the strap slot 148. As a result, the body 144 area of the D-ring is flexible whereas the reinforced area 146 may result in a semi-rigid or rigid section of the D-ring such that the D-ring does not yield to the anatomy of the wearer or brace upon which it is secured. On the other hand, the reinforced area 146 may be configured with a thickness allowing some flexibility to allow the D-ring to conform to the anatomy of the wearer or brace upon which it is secured.

The D-rings described herein may be constructed and formed in any manner described herein in connection to the subshells, and in any other manner known to the skilled person. It will be noted that the D-rings can be formed from rigid or semi-rigid material, as well as material that is flexible.

Figure 14:
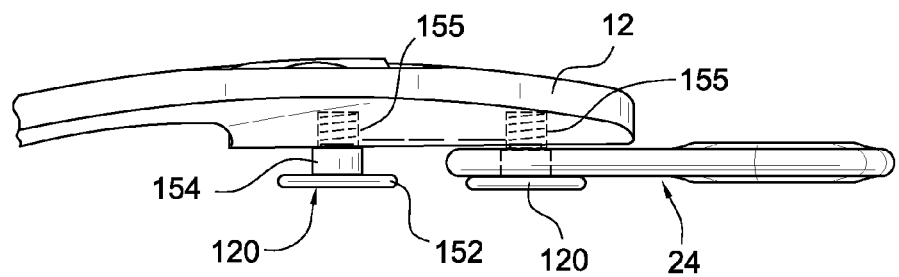
FIG. 14 is a schematic view showing attachment of the D-ring of FIG. 13 on one of a plurality anchoring members on an orthopedic device.

FIG. 14 depicts an anchoring member 120 having a cap 152 and a stem 154 upon which the cap 152 is secured. The cap 152 is arranged to penetrate the head portion 130 of the locking element 114 and rest along the insert region 136 when the anchoring member 120 is in the engaging opening 126. The cap 152 has a size less than the width of the receiving portion 124 but greater than the width of the engaging opening 126. The engaging opening 126 is proximate in size to the stem 154 and smaller in size than the cap 152. The engaging opening 126 prevents passage of the cap 152 therethrough.

Figures 15, 16:
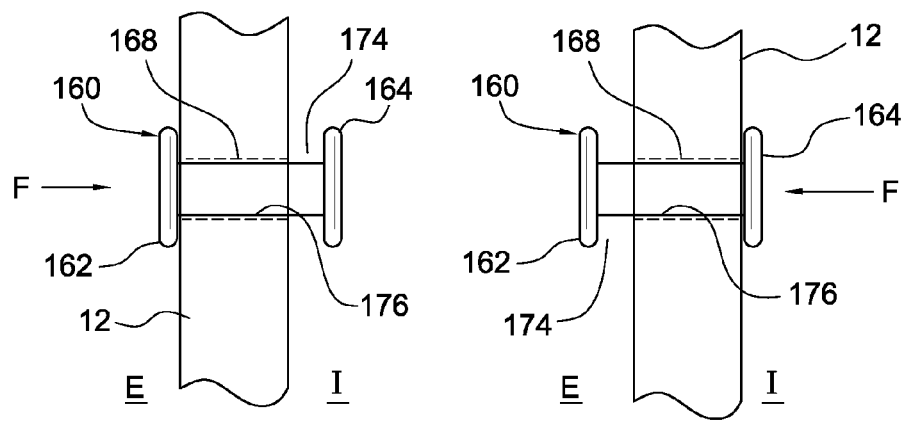
FIG. 15 is a schematic view showing a movable anchoring member in an interior mounted configuration.
FIG. 16 is a schematic view of the anchoring member of FIG. 15 in an exterior mounted configuration.

According to the embodiment and schematic views of FIGS. 15 and 16, an anchoring member 160 is adjustably movable to exterior E or interior I positions. The frame element, such as the upper frame element 12 of FIG. 1, has a thickness through which a channel or hole 168 is formed. The anchoring member 160 includes exterior and interior caps 162, 164, with a stem 176 extending therebetween. The stem 176 is sized longer than the channel 168 so the anchoring member 160 is slidable within the channel 168 between the exterior and interior sides. The caps 162, 164 have a diameter greater than the diameter of the channel 168 to they are retained by exterior and interior surfaces of the frame element.

When the anchoring member 160 is pressed with a force F fully toward either the exterior E or interior I surface of the frame element 12, a gap 174 is formed between the one of the surfaces of the frame element 12 and one of the caps 162, 164. The gap 174 is sized and configured to snugly receive a D-ring, such as the D-ring discussed above in reference to FIGS. 13 and 14, as shown in FIG. 17.

Figure 17:
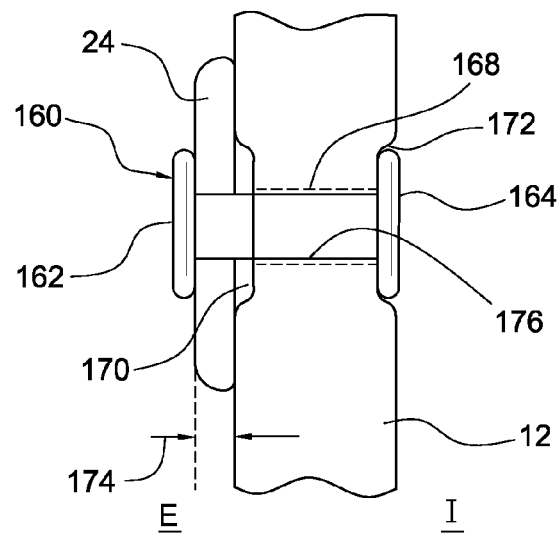
FIG. 17 is a schematic view showing a variation of the anchoring member on a frame element when secured with a D-ring.

FIG. 17 shows a variation of the embodiment of FIGS. 15 and 16, the frame element 12 may define recesses 170, 172 that are sized larger in diameter than the caps 160, 162, and have a depth greater than the thickness of the caps 160, 162. The recesses 170, 172 allow for the caps 160, 162 to form a flush surface in combination with both the exterior or interior surfaces depending on the configuration of the anchoring member 160, and the side upon which the D-ring 24 is mounted.

It will be noted that the anchoring member 160 is not limited for use with a D-ring, but it can be used with any number of subshell attachments for the orthopedic device, and be located at any number of locations along the frame of an orthopedic device.

Figure 18:
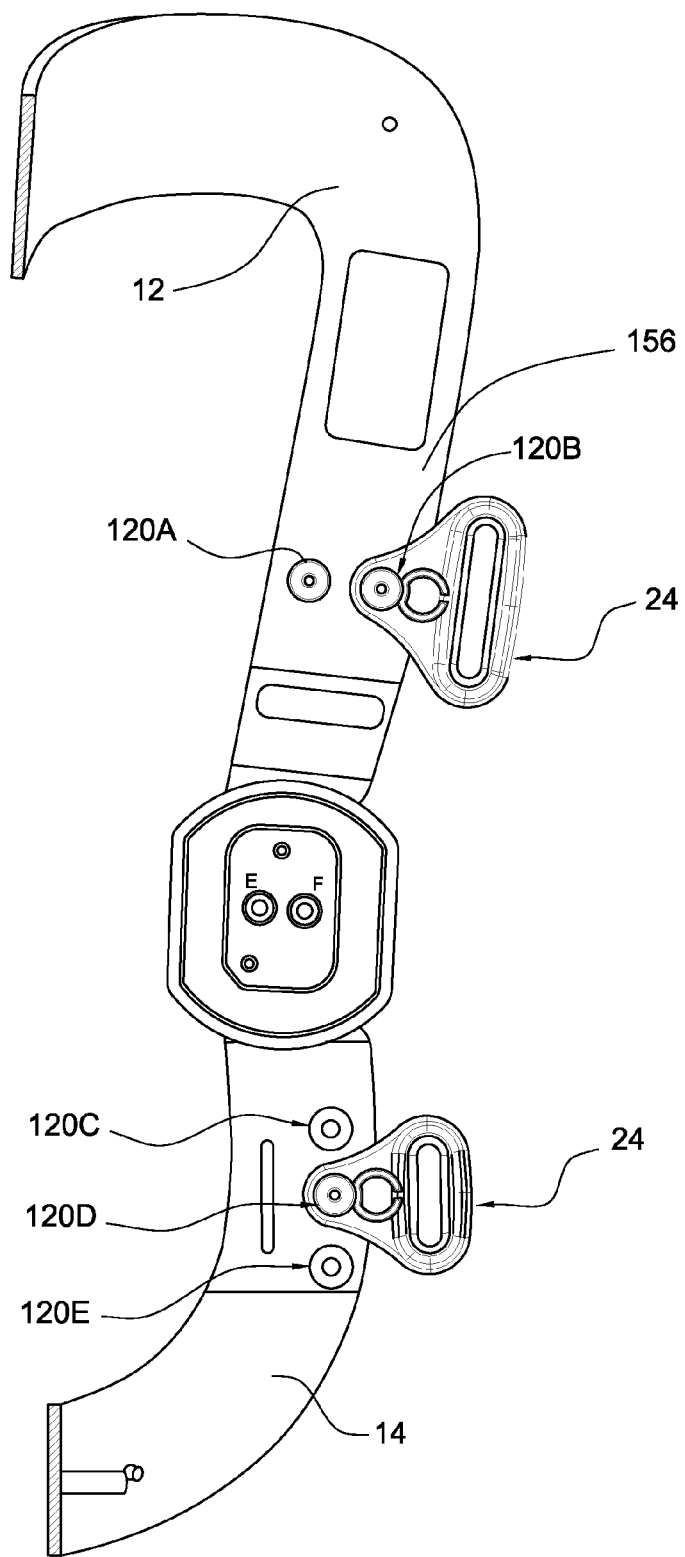
FIG. 18 is a sectional view taken along line XVIII-XVIII in FIG. 1.

FIG. 18 illustrates a variation of an interior surface 156 (as opposed to the depiction of exterior surfaces in FIG. 1) of the frame elements from which the anchoring members 120 extend. The anchoring members 120A, 120B are arranged in a substantially horizontal configuration, whereas anchoring members 120C, 120D, 120E are arranged in a substantially vertical configuration. Advantageously, the tibital strap can be mounted at a variety of heights along the uprights of the frame elements. Other configurations are available as would be considered necessary by the skilled person.

The anchoring members may be formed integrally with the frame elements or secured to the frame elements with conventional fastening members, such as screws or welding.

While the foregoing embodiments have been described and shown, it is understood that alternatives and modifications of these embodiments, such as those suggested by others, may be made to fall within the scope of the invention. While the orthopedic device has been described in the context of a knee brace, it will be understood that any of the principles described herein may be extended to other types of orthopedic devices.

The invention claimed is:

1. An orthopedic device, comprising:
   first and second frame elements being substantially rigid and located on opposite one another;
   a shell adjustably mounted on at least one strap secured to the first and second frame elements, the shell movably secured along the at least one strap and constructed from a flexible polymeric material, the shell including a pad mounted on an interior surface, the shell defining an upper periphery having a recessed portion arranged to correspond to anatomy of a wearer and peak portions located on opposed sides of the recessed portion to conform to the anatomy of the wearer's anatomy;
   a lateral frame element extending between the first and second frame elements arranged in an upright manner, the shell extending above the lateral frame element;
   a liner extending along a rear side of the lateral frame element, the liner further extending toward the shell and connecting to the shell such that the shell is incorporated with the liner;
   wherein a border portion of the liner extends beyond peripheral edges of the shell and a rear portion of the shell is covered by the liner.

2. The orthopedic device of claim 1, wherein the at least one strap includes first and second straps secured to first and second sides of the shell, respectively, and secured to the first and second frame elements respectively.

3. The orthopedic device of claim 2, wherein the shell is adjustable in position relative to the first and second frame element such that the shell is closer to the first frame element than the second frame element.

4. The orthopedic device of claim 1, wherein the shell is solely carried by the at least one strap.

5. The orthopedic device of claim 1, wherein the liner includes a stem bridging a portion extending along the lateral frame to a portion over which the shell extends.

6. The orthopedic device of claim 1, further comprising a compliant anti-migration wrap configured on the lateral frame element, the anti-migration wrap defining a portion having a shape of the lower frame element and opposed first and second sides proximate to the shell that secure to one another.

7. The orthopedic device of claim 6, wherein the anti-migration wrap has a first side defining a longer length extending freely from the lateral frame element and is arranged to wrap circumferentially about the anatomy of a wearer.

8. The orthopedic device of claim 1, wherein the at least one strap is a single strap secured to the first and second frame elements and having first and second ends adjustably securing to first and second sides of the shell.

9. The orthopedic device of claim 8, wherein the first and second sides of the shell define first and second slots, respectively, for securing to the single strap.

10. The orthopedic device of claim 1, wherein the at least one strap is substantially inelastic.

11. The orthopedic device of claim 1, wherein the shell defines a lateral portion extending along at least a segment of a rear surface of the lateral frame element, and the shell further including a stem extending upwardly from the lateral portion and a main body portion extending from the stem and defining the upper periphery, the main body configured and dimensioned wider than the stem.

12. The orthopedic device of claim 11, wherein the at least one strap has a first end secured to the first frame element, the at least one strap extending over an exterior surface of the shell, the strap securing to the second frame element, with a second end of the at least one strap extending freely relative to the second frame element.

13. The orthopedic device of claim 12, wherein the second end of the at least one strap includes a fastener securable to a front surface of the strap so that pressure may be exerted over the subshell and is directed toward anatomy of the wearer over the shell.

14. The orthopedic device of claim 12, wherein both the first and second ends of the at least one strap are securable over the exterior surface of the strap.

15. An orthopedic device, comprising:
   first and second frame elements being substantially rigid and located on opposite one another;
   a shell adjustably mounted on at least one substantially inelastic strap secured to the first and second frame elements, the shell movably secured along the at least one strap and constructed from a flexible polymeric material;
   wherein the shell is adjustable in position relative to the first and second frame element such that the shell is closer to the first frame element than the second frame element;
   wherein the at least one strap is a single strap secured to the first and second frame elements and having first and second ends adjustably securing to first and second sides of the shell;
   wherein the first and second sides of the shell define first and second slots, respectively, for securing to the single strap;
   a lateral frame element extending between the first and second frame elements arranged in an upright manner, the shell extending above the lateral frame element;
   a liner extending along a rear side of the lateral frame element, the liner further extending toward the shell and connecting to the shell such that the shell is incorporated with the liner;
   wherein a border portion of the liner extends beyond peripheral edges of the shell and a rear portion of the shell is covered by the liner.

16. An orthopedic device, comprising:
   first and second frame elements being substantially rigid and located on opposite one another;
   a shell adjustably mounted on at least one strap secured to the first and second frame elements, the shell movably secured along the at least one strap and constructed from a flexible polymeric material, the shell including a pad mounted on an interior surface, the shell defining an upper periphery having a recessed portion arranged to correspond to anatomy of a wearer and peak portions located on opposed sides of the recessed portion to conform to the anatomy of the wearer's anatomy;
   a lateral frame element extending between the first and second frame elements arranged in an upright manner, the shell extending above the lateral frame element;

a liner extending along a rear side of the lateral frame element, the liner further extending toward the shell and connecting to the shell such that the shell is incorporated with the liner;

wherein a front side of the shell is exposed and uncovered by the liner, the liner extending over an entirety of a rear side of the shell.

* * * * *